United States Patent [19]

Mifune et al.

[11] 4,272,606
[45] Jun. 9, 1981

[54] METHOD OF FORMING A HIGH-CONTRAST PHOTOGRAPHIC IMAGE

[75] Inventors: Hiroyuki Mifune; Shunji Takada; Yoshitaka Akimura; Yoshiharu Fuseya, all of Minami-ashigara, Japan

[73] Assignee: Fuji Photo Film Co., Ltd., Minami-ashigara, Japan

[21] Appl. No.: 117,882

[22] Filed: Feb. 1, 1980

Related U.S. Application Data

[63] Continuation-in-part of Ser. No. 903,336, May 5, 1978, abandoned.

[51] Int. Cl.³ .................................................. G03C 5/30
[52] U.S. Cl. ........................................ 430/264; 430/267; 430/423; 430/425; 430/438; 430/439; 430/440; 430/441; 430/442; 430/445; 430/446; 430/599; 430/600; 430/603; 430/949
[58] Field of Search .............. 430/423, 425, 438, 439, 430/440, 441, 442, 445, 446, 599, 600, 603, 264, 949

[56] References Cited

U.S. PATENT DOCUMENTS

| | | | |
|---|---|---|---|
| 3,386,831 | 6/1968 | Honig | 96/109 |
| 3,730,727 | 5/1973 | Olivares et al. | 96/95 |
| 3,782,949 | 1/1974 | Olivares et al. | 96/95 |

*Primary Examiner*—Mary F. Downey
*Attorney, Agent, or Firm*—Sughrue, Rothwell, Mion, Zinn and Macpeak

[57] ABSTRACT

A method of forming an extremely high-contrast negative photographic image which comprises image-wise exposing a photographic light-sensitive material comprising a support having thereon a mono-disperse silver halide emulsion layer containing surface latent image type silver halide grains and also containing a compound represented by the following general formula (1):

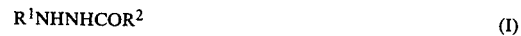

$$R^1NHNHCOR^2 \qquad (I)$$

wherein $R^1$ represents an aryl group, $R^2$ represents a hydrogen atom, a phenyl group or an unsubstituted alkyl group having 1 to 3 carbon atoms, and then processing the exposed light-sensitive material in the presence of a compound having a thioamido moiety in the molecule thereof.

22 Claims, No Drawings

METHOD OF FORMING A HIGH-CONTRAST PHOTOGRAPHIC IMAGE

CROSS REFERENCE OF THE RELATED APPLICATION

This application is a continuation-in-part of application Ser. No. 903,336 filed May 5, 1978 now abandoned.

BACKGROUND OF THE INVENTION

1. Field of the Invention

This invention relates to a method of image formation and, more specifically, to a method of forming extremely high contrast negative photographic images.

2. Description of the Prior Art

A method of obtaining photographic characteristics of a high contrast negative image by adding a hydrazine compound to a silver halide photographic emulsion is described in U.S. Pat. No. 2,419,975. U.S. Pat. No. 2,419,975 discloses that extremely high contrast photographic characteristics, such as a gamma ($\gamma$) of more than 10, can be obtained by adding a hydrazine compound to a silver chlorobromide emulsion and developing the emulsion with a developer having a pH as high as 12.8. However, strongly alkaline developers having a pH near 13 are so unstable that they tend to be oxidized by air and, therefore, cannot be used or stored for long periods of time. Moreover, development at such a high pH tends to cause fog.

U.S. Pat. No. 3,386,831 describes a process for stabilizing an emulsion by adding a mono-phenylhydrazide of an aliphatic carboxylic acid into an essentially surface-sensitive photographic silver halide emulsion. The object and effect of the invention disclosed in U.S. Pat. No. 3,386,831 is to stabilize the emulsion and it differs from the object and effect of the present invention.

Ultra high contrast photographic characteristics, either of a negative image or of a positive image, are very useful for the photographic reproduction of an image of a continuous tone comprising a dot image which is useful in making printing plates or the reproduction of a line image. For the above purposes, hitherto a method of using a silver chlorobromide photographic emulsion having a silver chloride content of more than 50 mol%, preferably more than 75 mol%, and developing the emulsion with a hydroquinone developer having an extremely reduced effective concentration of sulfite ions (usually less than 0.1 mol/l) has been generally adopted. However, in this method, since the sulfite ion in the developer is present at a low concentration, the developer is very unstable and cannot be stored for a period exceeding 3 days. Furthermore, since a silver chlorobromide emulsion containing a relatively high percentage of silver chloride must be used, high sensitivity cannot be obtained.

Accordingly, use of an emulsion of high sensitivity and a stable developer to obtain ultra high contrast photographic characteristics useful for the reproduction of a dot image or a line image have been strongly desired.

SUMMARY OF THE INVENTION

A first object of the present invention is to provide a method of forming extremely high contrast negative photographic images using a stable developer.

Another object of the present invention is to provide a method of forming extremely high contrast negative photographic images with a very small amount of exposure.

Still another object of the present invention is to provide a method of forming negative photographic images having an extremely high contrast and substantially free of fog.

The various objects of the present invention described above are achieved by image-wise exposing a silver halide photographic material comprising a support having thereon at least one negative image silver halide photographic emulsion layer, the emulsion layer containing mono-disperse silver halide grains substantially of the surface latent image type, and which contains in at least one hydrophilic colloid layer thereof a compound represented by the following general formula (I):

$$R^1NHNHCOR^2 \qquad (I)$$

wherein $R^1$ represents an aryl group, $R^2$ represents a hydrogen atom, a phenyl group or an unsubstituted alkyl group having 1 to 3 carbon atoms, and then processing the image-wise exposed photographic material in the presence of a compound having a thioamido moiety in the molecular structure thereof (hereinafter referred to as a thioamide compound, for simplicity).

DETAILED DESCRIPTION OF THE INVENTION

It has already been found that the formation of high contrast negative images can be achieved to some extent by the method disclosed in Japanese Patent Application No. 135562/1976 (disclosed in U.S. Patent Application Ser. No. 823,881, filed Aug. 11, 1977 and U.S. Patent Application Ser. No. 804,484, filed June 7, 1977), which comprises (i) using a photographic light-sensitive material which includes at least one silver halide photographic emulsion layer containing silver halide grains substantially of the surface latent image type and having an average grain size not exceeding 0.7 micron and a binder of up to 250 g per mol of the silver halide and in which either the emulsion layer or another hydrophilic colloid layer contains an organic acid hydrazide compound of a specific chemical structure, (ii) image-wise exposing the photographic material, and (iii) developing the exposed photographic material with a developing solution containing not less than 0.15 mol/l of sulfite ion at a pH between 11.0 and 12.3. The method of this invention provides the ability to obtain an extremely high contrast photographic image by using a very stable developer with a far lower amount of exposure.

In the general formula (I) above, $R^1$ represents a monocyclic or bicyclic aryl group. A suitable example of a monocyclic aryl group for $R^1$ is a phenyl group and a suitable example of a bicyclic aryl group for $R^1$ is a naphthyl group. The aryl group may be substituted with one or more substituents which are not electron-attracting, such as alkyl groups having 1 to 20 carbon atoms (which may be straight or branched chained, e.g., methyl, ethyl, propyl, isopropyl, n-butyl, isobutyl, n-octyl, n-hexyl, tert-octyl, n-decyl, n-dodecyl, etc.), aralkyl groups having 1 to 3 carbon atoms in the alkyl moiety thereof (e.g., benzyl, phenethyl, etc.), alkoxy groups having 1 to 20 carbon atoms (in which the alkyl moiety may be straight or branched chain, e.g., methoxy, ethoxy, 2-methylpropyoxy, etc.), amino groups which are mono- or disubstituted with alkyl groups having 1 to 20 carbon atoms, aliphatic acylamino groups having 2 to 21 carbon atoms or aromatic acylamino groups (e.g., acetylamino, octynylamino, benzoylamino, dimethylamino, etc.), etc.

$R^2$ represents a hydrogen atom, an unsubstituted alkyl group having 1 to 3 carbon atoms which may be straight or branched chained (e.g., methyl, ethyl, n-propyl, isopropyl) or a phenyl group.

The phenyl group may be substituted with one or more substituents which preferably are electron-attracting groups, such as a halogen atom (e.g., chlorine, bromine, etc.), a cyano group, a trifluoromethyl group, a carboxyl group or a sulfo group, etc.

Specific examples of suitable substituents represented by $R^1$ are a phenyl group, an α-naphthyl group, a β-naphthyl group, a p-tolyl group, an m-tolyl group, an o-tolyl group, a p-methoxyphenyl group, an m-methoxyphenyl group, a p-dimethylaminophenyl group, a p-diethylaminophenyl group, a p-(acetylamino)phenyl group, a p-(capryloylamino)phenyl group, a p-(benzoylamino)phenyl group and a p-benzylphenyl group.

Specific examples of suitable substituents represented by $R^2$, other than a hydrogen atom, are a methyl group, an ethyl group, an n-propyl group, an isopropyl group, a phenyl group, a 4-chlorophenyl group, a 4-bromophenyl group, a 3-chlorophenyl group, a 4-cyanophenyl group, a 4-carboxyphenyl group, a 4-sulfophenyl group, a 3,5-dichlorophenyl group and a 2,5-dichlorophenyl group.

The substituent represented by $R^1$ is preferably a monocyclic aryl group, and particularly preferred groups for $R^1$ are an unsubstituted phenyl group and a tolyl group.

The substituent represented by $R^2$ is preferably a hydrogen atom, a methyl group or a phenyl group which may be substituted. A hydrogen atom is particularly preferred for $R^2$.

Preferred compounds represented by the general formula (I) are those represented by the general formula (Ia):

$$R^1NHNHCOR^{12} \quad (Ia)$$

In this formula, $R^1$ has the same meaning as in the general formula (I), and $R^{12}$ represents a hydrogen atom, a methyl group, an unsubstituted phenyl group, or a phenyl group substituted with one or more electron-attracting groups.

Of the compounds represented by the above-described general formula (Ia), particularly preferred are compounds represented by the following general formula (Ib):

$$R^1NHNHCHO \quad (Ib)$$

In the above formula, $R^1$ has the same meaning as in the above-described general formula (I).

Of the compounds of the above general formula (Ib), the compounds represented by the following general formula (Ic) are especially preferred.

$$R^{11}NHNHCHO \quad (Ic)$$

In the above formula, $R^{11}$ represents an unsubstituted phenyl group or a tolyl group.

Specific examples of the compounds represented by the general formula (I) are given below, but this invention is not to be construed as being limited thereto.

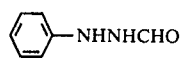 (I-1)

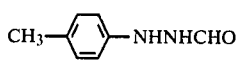 (I-2)

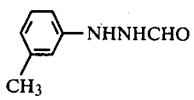 (I-3)

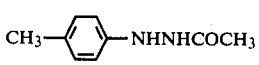 (I-4)

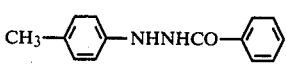 (I-5)

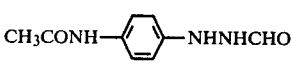 (I-6)

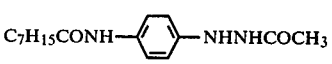 (I-7)

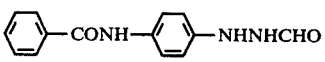 (I-8)

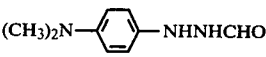 (I-9)

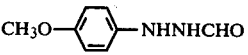 (I-10)

 (I-11)

 (I-12)

 (I-13)

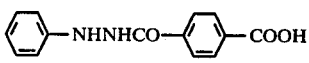 (I-14)

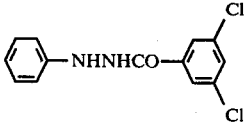 (I-15)

 (I-16)

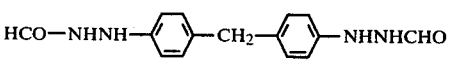

The compounds represented by the general formula (I) can be synthesized by reacting hydrazines with formic acid or by reacting hydrazines with acyl halides. Starting hydrazines such as

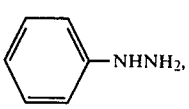

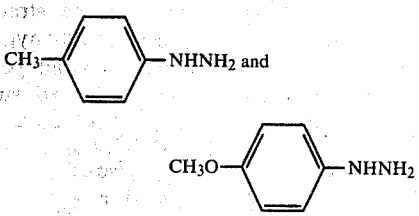

are commercially available and hydrazines of the formula

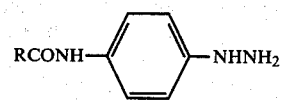

where R represents an aklyl group can be synthesized by reduction of a p-nitrophenylhydrazine. Suitable acyl halides which can be used include aliphatic acyl halides such as acetyl chloride, propionyl chloride, butyryl chloride, etc., and aromatic acyl halides such as benzoyl chloride, toluoyl chloride, etc. The reaction can be conducted in a solvent such as benzene, chloroform, pyridine, triethylamine, etc., and at a temperature of about 0° C. to about 100° C., preferably 0° C. to 70° C. A suitable molar ratio of the hydrazine to the acyl halide in the presence of a base such as pyridine or triethylamine which acts as a hydrogen halide acceptor for the hydrogen halide formed as a by-product ranges from about 1:1 to about 1:3, preferably 1:1.2 to 1:1.5 and in the absence of such a base ranges from about 1:0.3 to about 1:1, preferably 1:0.45 to 1:0.5. Hydrogen halide accepting agents such as triethylamine and pyridine can be employed in an amount of about 1 mol or more per mol of the acyl halide used.

Specific examples of the synthesis of the compounds of the general formula (I) are set forth below. Unless otherwise indicated herein, all parts, percents, ratios and the like are by weight.

SYNTHESIS EXAMPLE I (Synthesis of Compound (I-2))

110 g of formic acid was stirred at 25° to 30° C., and to this, 107 g of p-tolylhydrazine was gradually added. After completing the addition, heating was performed at 50° C. for 20 minutes while stirring the mixture. After cooling the mixture with ice, the resulting crystals were filtered out and recrystallized from 550 ml of acetonitrile to obtain 54.5 g of colorless needles having a melting point of 176° to 177° C.

SYNTHESIS EXAMPLE II (Synthesis of Compound (I-5))

15 g of p-tolylhydrazine was added to 100 ml of acetonitrile at 25° to 30° C. while stirring. Then, 15 g of benzoyl chloride was added dropwise at 25° to 30° C. After completing the addition, stirring was continued at 25° to 30° C. for 6 hours. After cooling the mixture with ice, the resulting crystals were filtered out and then recrystallized from benzene to obtain 7 g of colorless needles having a melting point of 146° C.

The compounds of the general formula (I) can be incorporated in the light-sensitive material used in the present invention in an amount of about $10^{-5}$ to about $10^{-1}$ mol/mol Ag. A more preferable range is from $5 \times 10^{-4}$ to $5 \times 10^{-2}$ mol/mol Ag.

The compound of the general formula (I) can be incorporated into the photographic emulsion using any methods employed for the addition of additives well-known in the photographic art. For example, when the compound is soluble in water, the compound can be dissolved in water in an appropriate concentration, and when the compound is insoluble or sparingly soluble in water, the compound can be dissolved in a suitable organic solvent which is miscible with water and which does not adversely affect the photographic characteristics, and the resulting solution is then added to the emulsion. Suitable organic solvents which can be used include, for example, alcohols, ethers, glycols, ketones, esters and amides. The compound can also be added in the form of dispersion as in the case of an oil soluble coupler.

As for the grain size distribution of the silver halide grains, 90% by weight or on a number basis of the total silver halide grains must have a grain size in a range of ±40% of the average grain size. In general, emulsions which satisfy the above-described requirement are referred to as a monodisperse emulsion in the photographic art.

The silver halide grains which are present in at least one silver halide emulsion layer in this invention are substantially surface latent image type silver halide grains. In other words, they are not substantially internal latent image type silver halide grains. The expression "substantially surface latent image type" silver halide grains as used in this specification means that the sensitivity obtained by (A) surface development is higher than that obtained by (B) internal development when development is carried out by (A) a surface development method and (B) an internal development method described below after exposure to light for 1 to 1/100 second. The sensitivity as used herein is defined as follows:

$$S = (100/Eh)$$

wherein S is the sensitivity, and Eh is the exposure amount required to obtain a density just intermediate between the maximum density ($D_{max}$) and the minimum density ($D_{min}$), i.e., $\frac{1}{2}(D_{max} + D_{min})$.

(A) Surface Development

Development is carried out at a temperature of 20° C. for 10 minutes in a developer of the following formulation.

N-Methyl-p-aminophenol (hemisulfate): 2.5 g
Ascorbic Acid: 10 g
Sodium Metaborate (tetrahydrate): 35 g
Potassium Bromide: 1 g
Water to make: 1 l

(B) Internal Development

After treatment at about 20° C. for 10 minutes in a bleaching solution containing 3 g/l of ferricyanide and 0.0125 g/l of phenosafranine and then washing for 10 minutes, development is carried out at 20° C. for 10 minutes in a developer of the following formulation.

N-Methyl-p-aminophenol (hemisulfate): 2.5 g
Ascorbic Acid: 10 g
Sodium Metaborate (tetrahydrate): 35 g
Potassium Bromide: 1 g
Sodium Thiosulfate: 3 g Water to make: 1 l Any of silver chloride, silver chlorobromide, silver iodochlorobromide, silver bromide and silver iodobromide can be used as the silver halide. Where silver chlorobromide or silver iodochlorobromide is used, the content of chloride should preferably be not more than about 80 mol%, and where silver iodobromide or silver iodochlorobromide is used, the iodide content should not exceed about 10 mol%. More preferably, the content of silver chloride should not exceed 50 mol% and the content of silver iodide should not exceed 6 mol%.

Since such a wide range of silver halide compositions can be employed in the method of the present invention, far higher photographic speeds can easily be achieved in comparison to conventional methods which are based on the so-called "lith" development.

Of compounds having a thioamido moiety

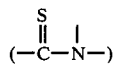

in the molecular structure, particularly effective thioamide compounds are those represented by the following general formula (II):

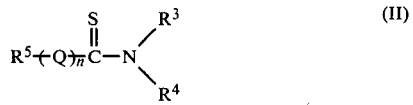

In the general formula (II), $R^5$ represents a hydrogen atom, an alkyl group (which may be straight chain, branched chain or cyclic), an aryl group (which may be mono- or bicyclic) or a heterocyclic group (which may be a 5- or 6-membered heterocyclic group containing one or more of a sulfur atom, a nitrogen atom or an oxygen atom as hetero atoms), and Q represents a sulfur atom, a selenium atom, an oxygen atom, a disulfide (—S—S—) group, —$NR^6$—,

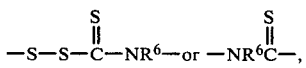

where $R^6$ has the same meaning as $R^5$, and n is 0 or 1.

$R^3$ and $R^4$ each represents a hydrogen atom, an alkyl group (which may be straight chain, branched chain or cyclic), an aryl group (which may be mono- or bicyclic), a heterocyclic group (which may be a 5- or 6-membered heterocyclic group containing one or more of a sulfur atom, a nitrogen atom or an oxygen atom as hetero atoms) or an amino group (which may be unsubstituted, monosubstituted or disubstituted). Alternatively, $R^5$ and $R^6$, $R^3$ and $R^4$, or $R^3$ and $R^5$ may combine to form a 5- or 6-membered nitrogen-containing heterocyclic ring, provided that neither of $R^4$ nor $R^6$ represents a hydrogen atom when $R^3$ and $R^5$ combine to form a 5- or 6-membered heterocyclic ring.

Suitable alkyl groups represented by $R^3$, $R^4$, $R^5$ and $R^6$ include alkyl groups having 1 to 20 carbon atoms which may be substituted. Suitable substituents include one or more of, for example, a halogen atom (e.g., chlorine, etc.), a cyano group, a carboxy group, a hydroxy group, an acyloxy group having 2 to 6 carbon atoms (e.g., alkylcarbonyloxy in which the alkyl moiety may be straight chain or branched chain, such as acetoxy, etc., or arylcarbonyloxy in which the aryl moiety may be mono- or bicyclic such as benzoyloxy, etc.), an alkoxycarbonyl group having 2 to 22 carbon atoms (e.g., in which the alkyl moiety may be straight chain or branched chain, such as ethoxycarbonyl, butoxycarbonyl, etc.), an aryl group (e.g., a monocyclic or bicyclic aryl group which may be substituted; such as phenyl, tolyl, p-sulfophenyl, etc.), etc. Preferred alkyl groups include a methyl group, an ethyl group, a propyl group (n- or iso-), a butyl group (n-, iso-, sec- or tert-), an amyl group (n-, iso-, sec- or tert-), a hexyl group, an octyl group, a dodecyl group, a pentadecyl group, a heptadecyl group, a chloromethyl group, a 2-chloroethyl group, a 2-cyanoethyl group, a carboxymethyl group, a 2-carboxyethyl group, a 2-hydroxyethyl group, a 2-hydroxyethyl group, a 2-acetoxyethyl group, an acetoxymethyl group, an ethoxycarbonylmethyl group, a butoxycarbonylmethyl group, a 2-methoxycarbonylethyl group, a benzyl group, an o-nitrobenzyl group and a p-sulfobenzyl group.

Suitable aryl groups represented by $R^3$, $R^4$, $R^5$ and $R^6$ are monocyclic and bicyclic aryl groups which may be substituted with one or more substituents. Monocyclic groups are preferred. Suitable substituents include, for example, an alkyl group having 1 to 20 carbon atoms (e.g., which may be straight chain or branched chain, such as methyl, ethyl, nonyl, etc.), an alkoxy group having 1 to 20 carbon atoms (e.g., in which the alkyl moiety may be straight chain or branched chain, such as methoxy, ethoxy, etc.), a hydroxy group, a halogen atom (e.g., chlorine, bromine, etc.), a carboxy group, a sulfo group, etc. Specific examples of suitable aryl groups are a phenyl group, a p-tolyl group, a p-methoxyphenyl group, a p-hydroxyphenyl group, a p-chlorophenyl group, a 2,5-dichlorophenyl group, a p-carboxyphenyl group, an o-carboxyphenyl group, a 4-sulfophenyl group, a 2,4-disulfophenyl group, a 2,5-disulfophenyl group, a 3-sulfophenyl group, a 3,5-disulfophenyl group, etc.

Suitable examples of 5- or 6-membered heterocyclic rings completed by $R^5$ and $R^6$ or $R^3$ and $R^4$ include a piperidine ring, a pyridine ring, a piperazine ring, a pyrimidine ring, a pyrrole ring, a pyrazole ring, an imidazole ring, a triazole ring, etc., with piperidine, pyridine, pyrrole, pyrimidine, piperazine and morpholine rings being preferred.

Suitable examples of 5- or 6-membered heterocyclic rings completed by $R^3$ and $R^5$ includes, for example, a thiazoline ring, a thiazolidine ring, a selenazoline ring, an oxazoline ring, an oxazolidine ring, an imidazoline ring, an imidazolidine ring, a pyrazoline ring, a pyrazolidine ring, a 1,3,4-thiadiazoline ring, a 1,3,4-oxadiazoline ring, a 1,3,4-triazoline ring, a tetrazoline ring, a thiohydantoin ring, a rhodanine ring, a dihydropyridine ring, a dihydropyrimidine ring, a dihydrotriazine ring, etc. These classes of heterocyclic rings described above, of course, include rings condensed with a 5 to 7-membered carbocyclic or heterocyclic ring; i.e., for thiazole, a benzothiazoline rings, a naphthothiazoline ring, a dihydronaphthothiazoline ring, a tetrahydrobenzothiazoline ring, etc.; for selenazole, a benzoselenazoline ring, etc.; for oxazoline, a benzoxazoline ring, a naphthoxazoline ring, etc.; for imidazoline, a benzimidazoline ring, a dihydroimidazolopyrimidine ring, etc.; for triazoline, a dihydrotriazolopyridine ring, a dihydrotriazolopyrimidine ring, etc.; for pyrazoline, a dihydropyrazolopyridine ring, a dihydropyrazolopyrimidine ring; etc.; for dihydropyrimidine, a dihydropyrazolopyrimidine ring, a dihydropyrrolopyrimidine ring, a dihydrotriazolopyrimidine ring, etc.

The carbon atoms of these heterocyclic rings can be substituted with a variety of substituents including, for example, an alkyl group having from 1 to 20 carbon atoms (e.g., which may be straight chain or branched chain, such as methyl, ethyl, n-butyl, t-butyl, heptyl, heptadecyl, etc.), an alkoxy group having 1 to 20 carbon atoms (e.g., in which the alkyl moiety may be straight chain or branched chain, such as methoxy, ethoxy, dodecyloxy, heptadecyloxy, etc.), an alkylthio group having 1 to 20 carbon atoms (e.g., in which the alkyl moiety may be straight chain or branched chain, such as methylthio, ethylthio, butylthio, etc.), a hydroxy group, a mercapto group, an amino group (which may be unsubstituted or mono- or disubstituted, e.g., alkyl-substituted amino groups, such as dimethylamino, methylamino, diethylamino, butylamino, benzylamino, etc., aryl-substituted amino groups such as anilino, diphenylamino, etc., acylamino groups, e.g., alkylcarbonylamino groups, arylcarbonylamino groups, alkylsulfonylamino groups or arylsulfonylamino groups, such as acetylamino, capryloylamino, benzoylamino, methylsulfonylamino, benzenesulfonylamino, p-toluenesulfonylamino, etc., and thioamido groups such as acetylthioamido, propionylthioamido, etc.), an aryl group (e.g., which may be mono- or bicyclic such as phenyl, naphthyl, tolyl, etc.), an alkenyl group having 2 to 20 carbon atoms (e.g., in which the alkyl moiety may be straight chain or branched chain, such as allyl, methallyl, etc.), an aralkyl group in which the alkyl moiety has 1 to 4 carbon atoms (e.g., benzyl, phenethyl, etc.), a halogen atom (e.g., chlorine, bromine, etc.), a cyano group, a carboxyl group, a sulfo group, a carbamoyl group (which can be substituted, such as carbamoyl, methylcarbamoyl, dimethylcarbamoyl, ethylcarbamoyl, phenylcarbamoyl, etc.), a thiocarbamoyl group (which can be substituted, e.g., thiocarbamoyl, methylthiocarbamoyl, dimethylthiocarbamoyl, ethylthiocarbamoyl, phenylthiocarbamoyl, etc.), an alkoxycarbonyl group having 2 to 22 carbon atoms (e.g., in which the alkyl moiety may be straight chain or branched chain, such as methoxycarbonyl, ethoxycarbonyl, butoxycarbonyl, etc.), an aryloxycarbonyl group (e.g., in which the aryl moiety may be mono- or bicyclic such as phenoxycarbonyl, etc.), an alkylcarbonyl group having 2 to 22 carbon atoms (e.g., in which the alkyl moiety may be straight chain or branched chain, such as acetyl, capryloyl, etc.), an oxo atom, etc. The above-described alkyl group may be substituted with a substituent such as a carboxyl group, a sulfo group, an alkoxycarbonyl group (e.g., in which the alkyl moiety may be straight chain or branched chain, such as methoxycarbonyl, ethoxycarbonyl, etc.), an acyloxy group (e.g., alkylcarbonyloxy in which the alkyl moiety may be straight chain or branched chain, such as acetoxy, etc., or arylcarbonyloxy in which the aryl moiety may be mono- or bicyclic such as benzoyloxy, etc.), an aryl group (e.g., in which the aryl moiety may be mono- or bicyclic, such as phenyl, substituted phenyl such as nitrophenyl, etc.), etc.

The nitrogen atom present in the above-described heterocyclic nuclei and capable of being substituted may be substituted with a substituent such as described in relation to $R^4$.

When Q represents an —$NR^4$—group, $R^4$ represents an alkyl group having 1 to 20 carbon atoms, which may be straight chain or branched chain and which may be substituted with one or more substituents. Suitable substituents include, for example, a halogen atom (e.g., chlorine, bromine), a cyano group, a carboxy group, a sulfo group, a sulfato group, a phospho group, a carbamoyl group, an aminosulfonyl group, a hydroxy group, an alkoxy group having 1 to 20 carbon atoms [e.g., in which the alkyl moiety may be straight chain or branched chain, such as methoxy, ethoxy, propoxy, butoxy, etc.; which may also be substituted with the following substituents: a hydroxy group, an alkoxy group having 1 to 6 carbon atoms (e.g., in which the alkyl moiety may be straight chain or branched chain, such as methoxy, ethoxy, propoxy, etc.), an acyloxy group having 2 to 8 carbon atoms (e.g., alkylcarbonyloxy in which the alkyl moiety may be straight chain or branched chain, such as acetoxy, propionoxy, etc., or arylcarbonyloxy in which the aryl moiety may be mono- or bicyclic such as benzoyloxy, etc.), a sulfo group, a sulfoalkoxy group having 1 to 6 carbon atoms (e.g., in which the alkyl moiety may be straight chain or branched chain, such as 2-sulfoethoxy, 3-sulfopropoxy, etc.), etc.], an acyloxy group having 2 to 22 carbon atoms, (e.g., alkylcarbonyloxy in which the alkyl moiety may be straight chain or branched chain, such as acetoxy, propionoxy, etc., or arylcarbonyloxy in which the aryl moiety may be mono- or bicyclic, such as benzoyloxy, etc.), an alkenyl group having 2 to 22 carbon atoms (e.g., vinyl, etc.), an alkoxycarbonyl group having 2 to 22 carbon atoms (e.g., in which the alkyl moiety may be straight chain or branched chain, such as methoxycarbonyl, ethoxycarbonyl, butoxycarbonyl, dodecyloxycarbonyl, etc.), an aryl group (which can be monocyclic or bicyclic an which can be substituted with examples being, e.g., phenyl, p-sulfophenyl, etc.), a heterocyclic ring (e.g., a thiazole, oxazole, imidazole, thiadiazole, oxadiazole, triazole, tetrazole, pyrimidine residue, etc.; with those particularly preferred being represented by

etc.

Specific examples of alkyl groups represented by $R^4$ include a methyl group, an ethyl group, a propyl group (n- or iso-), a butyl group (n-, sec-, iso- or tert-), an n-hexyl group, a dodecyl group, a heptadecyl group, a chloromethyl group, a 2-chloroethyl group, a 2-cyanoethyl group, a carboxymethyl group, a 2-carboxyethyl group, a 2-sulfoethyl group, a 3-sulfopropyl group, a 3-sulfobutyl group, a 4-sulfobutyl group, a 2-sulfatoethyl group, a 2-phosphoethyl group, a 2-hydroxyethyl group, a 3-hydroxypropyl group, a 2-methoxyethyl group, a 3-methoxypropyl group, a 2-ethoxyethyl group, a 2-(2-hydroxyethoxy)ethyl group, a 2-(2-acetoxyethoxy)ethyl group, a 2-(2-sulfoethoxy)ethyl group, a 2-[2-(3-sulfopropoxy)ethoxy]ethyl group, a 2-acetoxyethyl group, a 3-propionyloxybutyl group, an allyl group, a methoxycarbonylmethyl group, a 2-(methoxycarbonyl)ethyl group, a 4-(ethoxycarbonyl)butyl group, a butoxycarbonylmethyl group, a benzyl group, a 2-phenylethyl group, a p-sulfobenzyl group, a 2-(2-mercapto-3-benzimidazolyl)ethyl group, etc.

Of the compounds represented by the general formula (II), those represented by the following general formula (IIa) are particularly preferred.

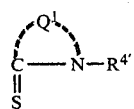
(IIa)

$Q^1$ represents the atoms necessary to complete a 5- or 6-membered heterocyclic ring. $R^{4'}$ represents the same groups as described for $R^4$ in the general formula (II) except for a hydrogen atom. Further, the atom in $Q^1$ adjacent the thioketo group does not have a hydrogen atom bonded thereto.

Specific examples of heterocyclic rings completed by $Q^1$ are the same as those formed by $R^3$ and $R^5$ in the formula (I). In addition thereto, the heterocyclic nucleus represented by $Q^1$ can be a nucleus containing a divalent substituent such as a thioxo (=S) group, a benzylidene group, an ethylidene (CH₃CH=) group, a substituted ethylidene group (e.g., benzoxazolylideneethylidene, thiazolinylideneethylidene, pyridylideneethylidene, quinolylideneethylidene, etc.), heterocyclic divalent residues (e.g., benzoxazolylidene, benzothiazolylidene, thiazolinylidene, pyridylidene, quinolylidene, etc.), etc.

The thioamide compounds represented by the general formula (II) can be synthesized using the methods disclosed in Japanese Patent Publication No. 34169/1973 (Compound Example Nos. 1 to 10, No. 49 and No. 50), *Journal of Pharmacology* (*Yakugaku Zasshi*), 74, pp. 1365-1369 (1954) (Compound Example Nos. 11 and 12), Japanese Patent Publication 23368/1974 (Compound Example Nos. 13, 21, 51 and 52), *Beilstein*, XII, 394, ibid., IV, 121 (Compound Example Nos. 16 and 17), Japanese Patent Publication No. 18008/1972 (Compound Example Nos. 18 and 19), U.S. Pat. No. 2,177,402 and U.S. Pat. No. 2,177,403 (Compound Example No. 38), Japanese Patent Publication No. 34168/1973 (Compound Example No. 40), British Patent No. 1,352,532 (Compound Example No. 54), *Monatsh*, 25, p. 167 (1904), *Journal of Chemical Society*, pp. 361-364 (1937) (Compound Example No. 57), *Journal of Organic Chemistry*, 26, pp. 3980-3987 (1961) (Compound Example No. 55), etc.

Some specific examples of thioamide compounds are listed below. However, the present invention is not to be construed as being limited to the following compounds.

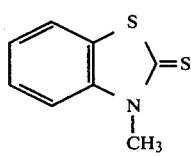
(II-1)

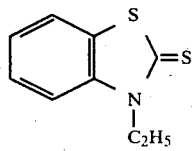
(II-2)

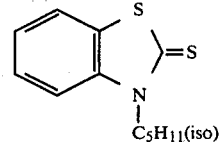
(II-3)

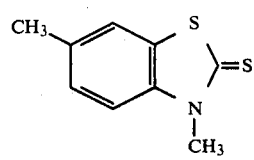
(II-4)

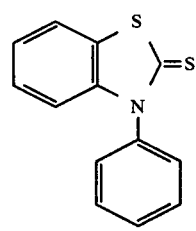
(II-5)

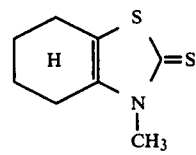
(II-6)

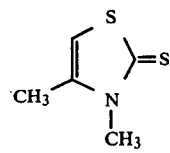
(II-7)

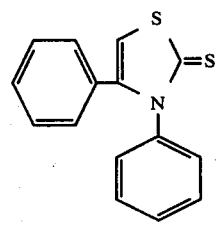
(II-8)

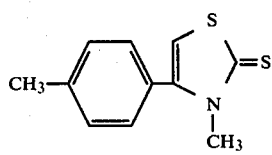
(II-9)

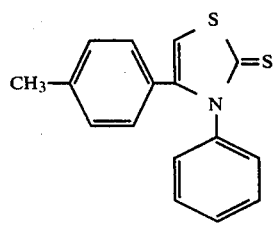
(II-10)

-continued
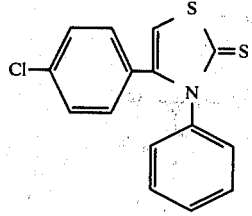 (II-11)
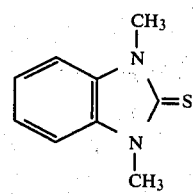 (II-12)
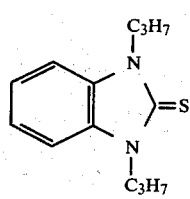 (II-13)
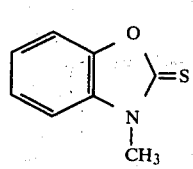 (II-14)
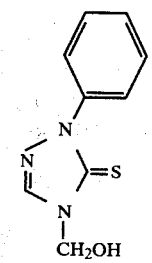 (II-15)
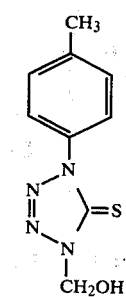 (II-16)
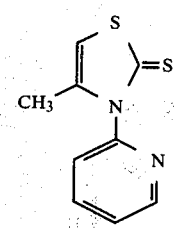 (II-17)
-continued
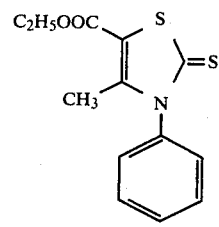 (II-18)
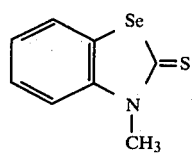 (II-19)
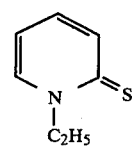 (II-20)
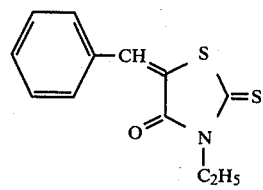 (II-21)
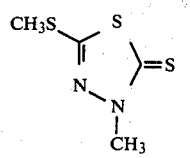 (II-22)
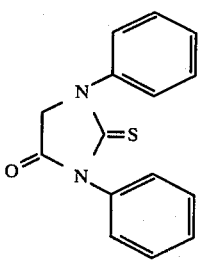 (II-23)
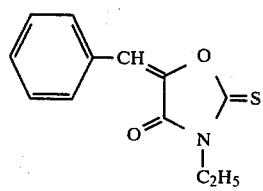 (II-24)
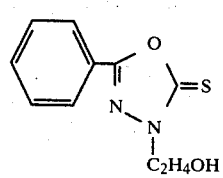 (II-25)

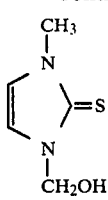 (II-26)
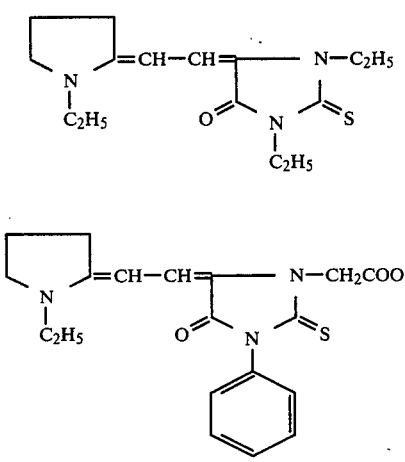 (II-27)
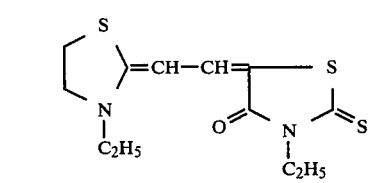 (II-28)
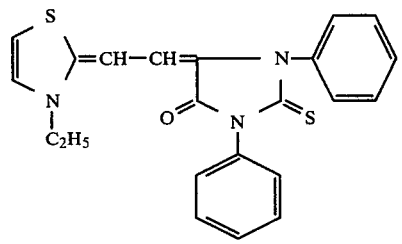 (II-29)
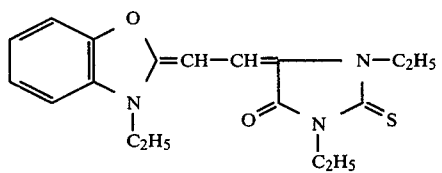 (II-30)
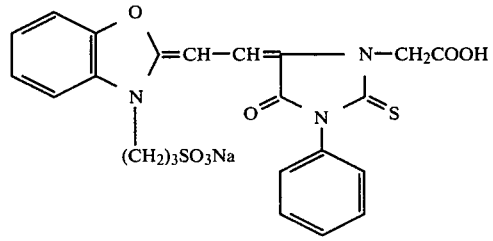 (II-31)
(II-32)
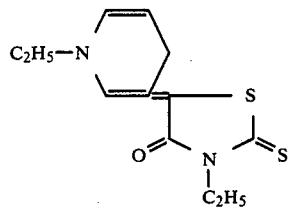 (II-33)
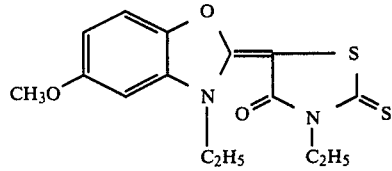 (II-34)
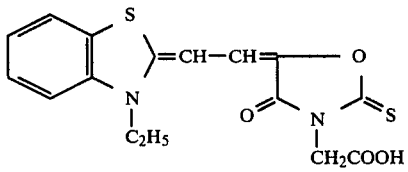 (II-35)
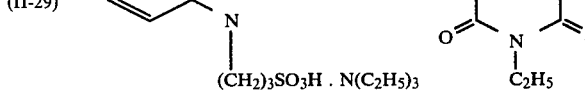 (II-36)
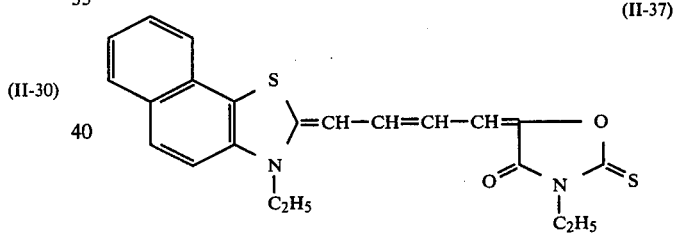 (II-37)
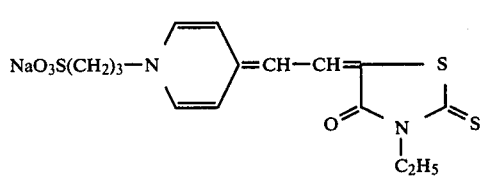 (II-38)
 (II-39)
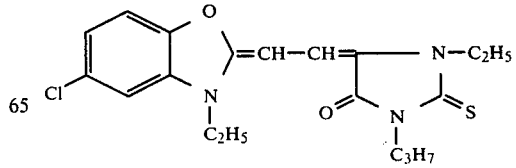 (II-40)

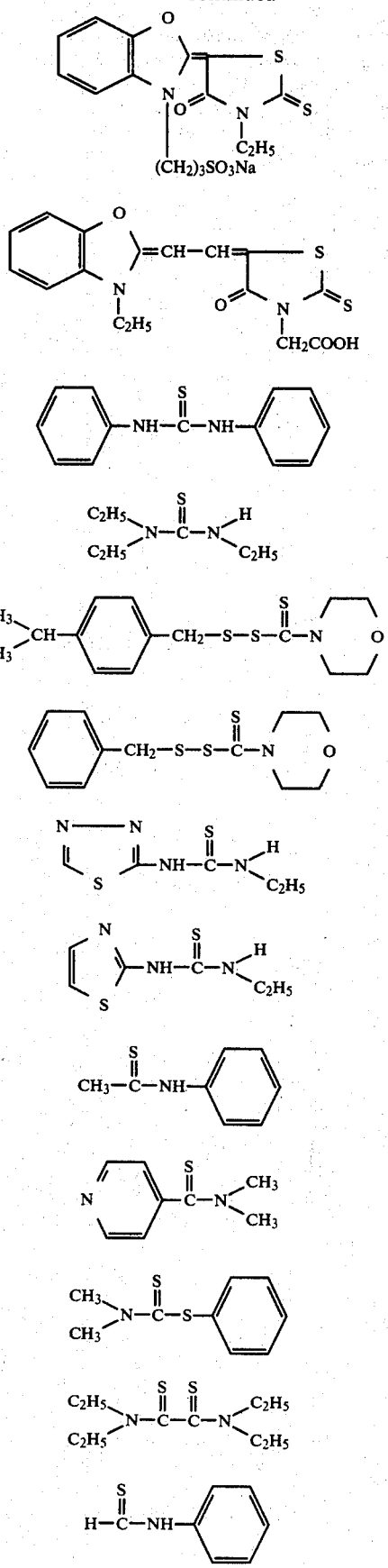
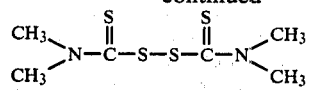

In the present invention, a thioamide compound can be incorporated into at least one of the hydrophilic colloid layers present in the light-sensitive material. Examples of suitable hydrophilic colloid layers include, in addition to the photographic emulsion layers, a protective layer, an intermediate layer, a filter layer, an antihalation layer, etc. Most favorably, the thioamide compound is present in a silver halide photographic emulsion layer comprising surface latent image type silver halide grains together with the compound represented by the general formula (I).

However, it is also possible to use other types of emulsions, and the thioamide compound can be present in one emulsion layer or in two or more different emulsion layers. The thioamide compound is preferably present in an amount of about $10^{-6}$ to about $5 \times 10^{-2}$, and more preferably $3 \times 10^{-5}$ to $10^{-2}$ mol, per mol of silver present in the equivalent coated area. The amount can be optimized depending on various factors such as the grain size of the silver halide, the halogen composition of the silver halide, the method and degree of chemical sensitization, the spacial relationship between the photographic emsulsion layer and the layer in which the thioamide compound is incorporated, the chemical species of anti-foggant, etc. Test procedures which can be used for such optimization are routine and well known in the photographic art.

As is the case in adding a compound represented by the general formula (I) to a photographic emulsion, the thioamide compound can be added to a photographic emulsion or coating mixtures used to produce other light-insensitive hydrophilic colloid layers in the form of a solution. More specifically, such a solution can be prepared using a water-miscible organic solvent such as an alcohol (e.g., methanol, ethanol, etc.), a ketone (e.g., acetone), an ester (e.g., ethyl acetate), etc., or with water when the compound is soluble in water. Use of an alkaline or acid aqueous solution is advantageous in some cases.

Where the thioamide compound is incorporated into the photographic emulsion, the compound can be added at any time between the beginning of chemical ripening to the coating. More preferably, the thioamide compound should be added after the completion of the chemical ripening, and most preferably the thioamide compound should be added to the coating mixture prepared ready for coating.

Alternatively, the thioamide compound can be incorporated into the developing solution. The thioamide compound is dissolved in a suitable solvent such as a watermiscible organic solvent, e.g., an alcohol (e.g., methanol and ethanol), a ketone (e.g., acetone and methyl ethyl ketone), an ester (e.g., ethyl acetate), and water to form a solution, which is added during preparation of the developer or into the finished developing solution. The solution described above may be alkaline or acid depending on the requirement involved.

Further, the exposed photographic material can be additionally treated with a bath containing the thioamide compound prior to development.

A suitable amount of the thioamide compound in the developer is about $10^{-7}$ to about $10^{-2}$ mol per liter of the developer, and more preferably $3 \times 10^{-6}$ to $5 \times 10^{-3}$ mol per liter of the developer.

The photographic emulsion used in this invention can be prepared using the methods described in, e.g., P. Grafkides, *Chimie et Physique Photographique,* Paul Montel, Paris (1967), G. F. Duffin, *Photographic Emulsion Chemistry,* The Focal Press, London (1966), V. L. Zelikman et al., *Making and Coating Photographic Emulsions,* The Focal Press, London (1964), etc. That is, any of the acid method, the neutral method, the ammonia method and other methods can be used. Moreover, a soluble silver salt can be reacted with a soluble halogen salt using any of the single jet method, the double jet method and a combination thereof.

The method in which grains are formed in the presence of an excess of silver ions (the so-called reverse mixing method) can also be used. As one of the modes of the double jet method, the method in which the pAg of the liquid phase in which the silver halide is to be produced is kept constant, that is, the so-called controlled double jet method, can be used. This method can provide silver halide emulsions having a regular crystal form and an almost uniform grain size.

The silver halide grains which can be used in the present invention have a mean grain size of greater than about $0.7\mu$. The term "mean grain size" is a well known and easily understandable technical term commonly used by those skilled in the art of silver halide photography. Where the grains are spherical or can be considered to be approximately spherical, the grain size means the grain diameter. With cubic grains, the edge length $$\sqrt[x]{\frac{4}{\pi}}$$

is taken as the grain size. The mean grain size is determined as an algebraic or geometric mean based on the projected areas of the grains. The details of a method for determining mean grain size are described in C. E. K. Mees and T. H. James, *The Theory of the Photographic Process,* 3rd Ed., pp. 36–43, Macmillan Co., New York (1966). A mean grain size of not more than $0.4\mu$ is more preferred. With the emulsion of the present invention, even though the mean grain size of the grains is small, a high sensitivity can be obtained.

The silver halide grains in the photographic emulsion may be regular crystals such as cubic crystals or octahedral crystals, or irregular crystals such as spherical crystals or plate crystals, or may have a composite crystal form of these crystal forms. The grains may comprise mixed grains having various crystal forms.

The interior and the surface layer of the silver halide grain may be different or the grains may be uniform throughout.

In the process of the formation of the silver halide grains or physical ripening, cadmium salts, zinc salts, lead salts, thallium salts, rhodium salts or complex salts thereof, iron salts or iron complex salts, and the like can be present.

Two or more silver halide emulsions which are separately prepared can be mixed and then used, if desired.

Gelatin can be advantageously used as the binder or protective colloid for the photographic emulsion used in this invention. However, other hydrophilic colloids can be used as well. For example, proteins such as gelatin derivatives, graft polymers between gelatin and other high polymers, albumin, casein, etc.; cellulose derivatives such as hydroxyethyl cellulose, carboxymethyl cellulose, cellulose sulfates, etc.; saccharide derivatives such as sodium alginate, starch derivatives, etc.; and various synthetic hydrophilic high polymers of homo- or copolymers such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc., can be used as the binder or protective colloid for the photographic emulsion.

Acid-processed gelatin may be used as well as lime-processed gelatin as the gelatin. In addition, the hydrolyzed products of gelatin and enzyme-decomposed products of gelatin are also suitable. Suitable gelatin derivatives which can be used include those obtained by reacting gelatin with various compounds such as acid halides, acid anhydrides, isocyanates, bromoacetic acid, alkanesulfones, vinylsulfonamides, maleinimides, polyalkylene oxides, epoxy compounds, etc. Specific examples thereof are described in U.S. Pat. Nos. 2,614,928, 3,132,945, 3,186,846, 3,312,553, British Pat. Nos. 861,414, 1,033,189, 1,005,784, Japanese Patent Publication No. 26845/67.

As the above-described gelatin graft polymer, those which are obtained by grafting homo- or copolymers of vinyl monomers such as acrylic acid, methacrylic acid, the ester or amide derivatives thereof, acrylonitrile, styrene, etc., to gelatin can be used. In particular, graft polymers with a polymer having some compatibility with gelatin, such as polymers of acrylic acid, methacrylic acid, acrylamide, methacrylamide, hydroxyalkyl methacrylates, etc., are preferred. Examples thereof are described in U.S. Pat. Nos. 2,763,625, 2,831,767, 2,956,884, etc. Typical synthetic hydrophilic materials are described in, e.g., West German Patent No. 2,312,708, U.S. Pat. Nos. 3,620,751, 3,879,205 and Japanese Patent Publication No. 7561/68.

The photographic silver halide emulsions of the present invention preferably contain less than about 250 g of binder per mol of silver halide. If the emulsions contain less than about 250 g of binder per mol of silver halide, it is possible to easily obtain a contrasty tone, and, particularly, to obtain an extremely contrasty photographic characteristic of a $\gamma$ of more than about 10 which is an object of the present invention.

After the formation of the precipitates or after physical ripening, the soluble salts are usually removed from the emulsion. For this purpose, the noodle washing method long well known in which gelatin is subjected to gelation may be used. Furthermore, the flocculation method which employs an inorganic salt having a polyvalent anion such as sodium sulfate, an anionic surface active agent, an anionic polymer (such as polystyrene sulfonic acid) or a gelatin derivative (such as an aliphatic acylated gelatin, an aromatic acylated gelatin or an aromatic carbamoylated gelatin) may be used. The removal of the soluble salts may be omitted, if desired.

Although the photographic silver halide emulsions used in the present invention need not necessarily be chemically sensitized, chemically sensitized silver halide emulsions are preferred. Processes for chemical sensitization of the silver halide emulsions which can be used include known sulfur sensitization, reduction sensitization and noble metal sensitization processes. These processes are described in references such as P. Grafkides, *Chimie et Physique Photographique,* Paul Montel, Paris (1967) or Zelikmann, *Making and Coating Photographic Emulsions,* The Focal Press, London (1964) or H. Friester, *Die Grundlagen der Photographischen Prozesse mit Silberhalogeniden*, Akademische Verlagsgesellschaft, (1968). In the noble metal sensitization processes, a gold sensitization process is a typical process where gold compounds or mainly gold complexes are used. A reduction sensitization process may be used if the process does not generate fog to a degree which causes practical difficulties. A preferred chemical sensitization process for the present invention is the use of a sulfur sensitization process.

Examples of sulfur sensitizing agents which can be used include not only sulfur compounds present in the gelatin per se but also various sulfur compounds such as thiosulfates, thioureas, thiazoles or rhodanines, etc. Examples of suitable sulfur compounds are described in U.S. Pat. Nos. 1,574,944, 2,410,689, 2,278,947, 2,728,668 and 3,656,955. Typical examples of reduction sensitizing agents which can be used include stannous salts, amines, formamidine sulfinic acid and silane compounds, etc., as described in U.S. Pat. Nos. 2,487,850, 2,518,698, 2,983,609, 2,983,610 and 2,694,637. Complex salts of Group VIII metals in the Periodic Table, such as gold, platinum, iridium or palladium, etc., can be used for noble metal sensitization and examples thereof are described in U.S. Pat. No. 2,448,060 and British Patent No. 618,061, etc.

The silver halide emulsion layers or other hydrophilic colloid layers in the light-sensitive material of this invention can contain an anti-fogging agent such as 1,2,3-triazole compounds (particularly benzotriazoles), benzothiazolium compounds, etc.

The effect of this invention is enhanced even more by adding a small amount of an iodide (such as potassium iodide) to the emulsion after the formation of the grains, before chemical ripening, after chemical ripening or before coating. A suitable amount of the iodide added ranges from about $10^{-4}$ to about $10^{-2}$ mol/mol Ag.

The photographic emulsions used in this invention can be spectrally sensitized with methine or other dyes. Suitable sensitizing dyes include cyanine dyes, merocyanine dyes, complex cyanine dyes, complex merocyanine dyes, holopolar cyanine dyes, hemicyanine dyes, styryl dyes and hemioxonol dyes. Particularly useful dyes are cyanine dyes, merocyanine dyes and complex merocyanine dyes. These dyes can contain, as a basic heterocyclic nucleus, any of the nuclei which are usually employed in cyanine dyes. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus and the like; these above-described nuclei condensed with an alicyclic hydrocarbon ring; and these above-described nuclei condensed with an aromatic hydrocarbon ring, such as an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus and a quinoline nucleus can be present. The carbon atoms of the above-described nuclei may be substituted.

The merocyanine dyes or complex merocyanine dyes can contain, as a nucleus having a ketomethylene structure, a 5- to 6-membered heterocyclic nucleus such as a pyrazolin-5-one nucleus, a thiohydantoin nucleus, a 2-thiooxazolidin-2,4-dione nucleus, a thiazolidin-2,4-dione nucleus, a rhodanine nucleus or a thiobarbituric acid nucleus.

Useful sensitizing dyes are those described in, e.g., German Patent No. 929,080, U.S. Pat. Nos. 2,231,658, 2,493,748, 2,503,776, 2,519,001, 2,912,329, 3,656,959, 3,672,897 and 3,694,217, British Patent No. 1,242,588, Japanese Patent Publication No. 14030/69, etc.

These sensitizing dyes may be used individually or as a combination thereof. A combination of sensitizing dyes is often employed particularly for the purpose of supersensitization. Typical examples of such combinations are described in, e.g., U.S. Pat. Nos. 2,688,545, 2,977,229, 3,397,060, 3,522,052, 3,527,641, 3,617,293, 3,628,964, 3,666,480, 3,679,428, 3,703,377, 3,769,301, 3,814,609 and 3,837,862, British Patent No. 1,344,281, Japanese Patent Publication No. 4936/68, etc.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic ring group (e.g., those described in U.S. Pat. Nos. 2,933,390 and 3,635,721 aromatic organic acid-formaldehyde condensates (e.g., those described in U.S. Pat. No. 3,743,510), azaindene compounds, and the like, can be present. The combinations described in U.S. Pat. Nos. 3,615,613, 3,615,641, 3,617,295 and 3,635,721 are particularly useful.

A water-soluble dye may be present in any of the hydrophilic colloid layers in the photographic light-sensitive material of this invention as a filter dye or for prevention of light scattering, antihalation or various other purposes. Examples of these dyes include oxonol dyes, hemioxonol dyes, styryl dyes, merocyanine dyes, cyanine dyes and azo dyes. Of them, oxonol dyes, hemioxonol dyes and merocyanine dyes are particularly useful. Specific examples of dyes which can be used are those described in British Patent Nos. 584,609 and 1,177,429, Japanese Patent Application (OPI) Nos. 85130/73, 99620/74 and 114420/74 (the term "OPI" as used herein refers to a "published unexamined Japanese patent application", hereinafter the same), and U.S. Pat. Nos. 2,274,782, 2,533,472, 2,956,879, 3,148,187, 3,177,078, 3,247,127, 3,540,887, 3,575,704, 3,653,905 and 3,718,472.

An inorganic or organic hardener may be present in any of the hydrophilic colloid layers in the light-sensitive material of this invention. For example, chromium salts (such as chrome alum or chromium acetate), aldehydes (such as formaldehyde, glyoxal or glutaraldehyde), N-methylol compounds (such as dimethylolurea or methyloldimethylhydantoin), dioxane derivatives (such as 2,3-dihydroxydioxane), active vinyl compounds (such as 1,3,5-triacryloyl-hexahydro-s-triazine or bis(vinylsulfonyl)methyl ether), active halogen compounds (such as 2,4-dichloro-6-hydroxy-s-triazine), mucohalic acids (such as mucochloric acid or mucophenoxychloric acid), isooxazoles, dialdehyde starch, 2-chloro-6-hydroxytriazinylated gelatin and the like can be used individually or in combination. Specific examples of these compounds are described in, e.g., U.S. Pat. Nos. 1,870,354, 2,080,019, 2,726,162, 2,870,013, 2,983,611, 2,992,109, 3,047,394, 3,057,723, 3,103,437, 3,321,313, 3,325,287, 3,362,827, 3,539,644 and 3,543,292, British Patent Nos. 676,628, 825,544 and 1,270,578, German Patent Nos. 872,153 and 1,090,427, Japanese Patent Publication Nos. 7133/69 and 1872/71, etc.

The light-sensitive material of this invention may contain various known surface active agents for various purposes, e.g., as a coating aid, for preventing the generation of static charges, improving slip characteristics, improving emulsion dispersion, preventing adhesion, improving photographic characteristics (e.g., accelerating development, increasing contrast, sensitizing), etc.

For example, nonionic surface active agents such as saponin (steroids), alkylene oxide derivatives (such as polyethylene glycol, polyethylene glycol/polypropylene glycol condensates, polyethylene glycol alkyl or alkylaryl ethers, polyethylene glycol esters, polyethylene glycol sorbitan esters, polyalkylene glycol alkylamines or amides or silicone-polyethlene oxide adducts), glycidol derivatives (such as alkenylsuccinic acid polyglycerides or alkylphenol polyglycerides), aliphatic esters of polyvalent alcohols, alkyl esters of sucrose, urethanes or ethers; anionic surface active agents containing an acidic group such as a carboxy group, a sulfo group, a phospho group, a sulfuric ester group or a phosphoric ester group, such as triterpenoid type saponin, alkylcarboxylates (salts), alkylsulfonates (salts), alkylbenzenesulfonates (salts), alkylnaphthalenesulfonates (salts), alkylsulfates, alkylphosphates, N-acyl-N-alkyltaurines, sulfosuccinates, sulfoalkylpolyoxyethylene alkylphenyl ethers or polyoxyethylene alkylphosphates; amphoteric surface active agents such as amino acids, aminoalkylsulfonic acids, aminoalkylsulfuric esters, aminoalkylphosphoric esters, alkylbetaines, amineimides or amine oxides; and cationic surface active agents such as alkylamine salts, aliphatic or aromatic quaternary ammonium salts (such as pyridinium or imidazolium salts) or phosphonium or sulfonium salts containing an aliphatic or heterocyclic ring can be used.

Specific examples of these surface active agents are described in, e.g., U.S. Pat. Nos. 2,240,472, 2,831,766, 3,158,484, 3,210,191, 3,294,540 and 3,507,660, British Patent Nos. 1,012,495, 1,022,878, 1,179,290 and 1,198,450, Japanese Patent Application (OPI) No. 117414/75, U.S. Pat. Nos. 2,739,891, 2,823,123, 3,068,101, 3,415,649, 3,666,478 and 3,756,828, British Patent No. 1,397,218, U.S. Pat. Nos. 3,133,816, 3,441,413, 3,475,174, 3,545,974, 3,726,683 and 3,843,368, Belgian Patent No. 731,126, British Patent Nos. 1,138,514, 1,159,825 and 1,374,780, Japanese Patent Publication Nos. 378/65, 379/65 and 13822/68, U.S. Pat. Nos. 2,271,623, 2,288,226, 2,944,900, 3,253,919, 3,671,247, 3,772,021, 3,589,906 and 3,754,924, German Patent Application (OLS) No. 1,961,638, Japanese Patent Application (OPI) No. 59025/75, etc.

The photographic emulsion of this invention can contain a dispersion of a synthetic polymer which is insoluble or slightly soluble in water for the purpose of improving the dimensional stability, or other purposes. Examples of polymers which can be used include polymers composed of one or more of an alkyl acrylate or methacrylate, an alkoxyalkyl acrylate or methacrylate, a glycidyl acrylate or methacrylate, an acryl or methacrylamide, vinyl esters (for example, vinyl acetate), acrylonitrile, olefins and styrene, etc., and polymers comprising a combination of the above-described monomers and acrylic acid, methacrylic acid, $\alpha,\beta$-unsaturated dicarboxylic acids, hydroxyalkyl acrylates or methacrylates or styrenesulfonic acid, etc. For example, those compounds described in U.S. Pat. Nos. 2,376,005, 2,739,137, 2,853,457, 3,062,674, 3,411,911, 3,488,708, 3,525,620, 3,607,290, 3,635,715 and 3,645,740, and British Patent Nos. 1,186,699 and 1,307,373 can be used. A suitable amount of the polymer ranges from about 20 to 80% by weight based on the total weight of the binders.

Since high contrast emulsions such as that of this invention are suitable for the reproduction of line drawings and the dimensional stability is of importance for such a purpose, it is preferred for the above-described polymer dispersion to be employed.

The photographic emulsions are coated on conventional supports which do not undergo serious dimensional changes during processing. Typical supports which can be used are a cellulose acetate film, a polystyrene film, a polyethylene terephthalate film, a polycarbonate film, a laminate thereof, paper, baryta paper, paper coated or laminated with a hydrophobic polymer such as polyethylene, polypropylene, etc., as are commonly used for photographic light-sensitive materials. Transparent supports can be employed for certain end-uses of the light-sensitive material. Also, transparent supports may be colored by adding a dye or a pigment thereto as described in *J. SMPTE*, 67, 296 (1958), etc.

Where adhesion between the support and the photographic emulsion layer(s) is insufficient, a subbing layer (an adhesive layer adhesive to both the support and the photographic emulsion layer(s)) is employed. Also, in order to improve the adhesion, the surface of the support may be subjected to a preliminary processing such as a corona discharge, irradiation with ultraviolet light, flame treatment, etc. A suitable coating amount of silver is about 0.5 g/m$^2$ to about 10 g/m$^2$ of the support.

Exposure to light for obtaining a photographic image can be performed in a usual manner. Various known light sources such as natural light (sunlight), a tungsten lamp, a fluorescent light, a mercury lamp, a xenon arc lamp, a carbon arc lamp, a xenon flash lamp or a cathode ray tube flying spot can be used. The exposure time can, of course, be about 1/1,000 sec to about 1 sec which is usually employed with cameras, and further, exposure for shorter than about 1/1,000 sec, for example, about 1/10$^4$ to about 1/10$^6$ sec which is employed in case of using a xenon flash lamp or a cathode ray tube, and exposure for longer than about 1 sec can be employed. If desired, the spectral composition of the light used for the exposure can be controlled using a color filter. The fluorescence resulting from the excitation of a phosphor caused by ionizing radiatiion or a laser beam can also be used for exposure. Moreover, exposure to electron radiation, X-rays, $\gamma$-rays or $\alpha$-rays may be employed.

The photographic light-sensitive material of this invention can be photographically processed using known methods and known processing solutions. The processing temperature usually ranges from about 18° to about 50° C., but temperatures lower than about 18° C. or higher than about 50° C. may be used. This invention is useful for the formation of an image by development in which a silver image is formed (a black-and-white photographic processing).

The developers used for black-and-white photographic processing preferably contain, as a developing agent, aminophenols (such as N-methyl-p-aminophenol), 3-pyrazolidones (such as 1-phenyl-3-pyrazolidone), 1-phenyl-3-pyrazolines, dihydroxybenzenes (such as hydroquinone), and combinations of a dihydroxybenzene (such as hydroquinone) and other of the afore-mentioned developing agents. Moreover, the developers usually contain a known antioxidant, an alkali agent, a pH buffer or the like and, if desired, a dissolving aid, a color toning agent, a development accelerator, a surface active agent, an anti-foaming agent, a water softener, a hardener, a tackifier, etc., may be present.

An anti-fogging agent (such as an alkali metal halide or benzotriazole) may be present in the developer.

According to this invention, even when development is carried out using a developer containing more than about 0.15 mol/l of sulfite ions, a γ of more than 8 can be obtained. The pH of the developer is preferably about 11 to about 12.3. If the pH exceeds about 12.3, the developer is unstable even when a high concentration of sulfite ions is present, and it is difficult to maintain stable photographic characteristics for more than 3 days under usual use conditions.

Those fixing solutions having a composition generally employed in the art can be used in the present invention. Not only thiosulfates and thiocyanates but also organic sulfur compounds known as fixing agents can be used as fixing agents in the present invention.

Suitable preferred examples of fixing agents which can be used in the fixing solution include water-soluble thiosulfates such as sodium thiosulfate, potassium thiosulfate, ammonium thiosulfate, etc., water-soluble thiocyanates such as sodium thiocyanate, potassium thiocyanate, ammonium thiocyanate, etc., water-soluble organic diol fixing agents containing an oxygen atom or a sulfur atom such as 3-thia-1,5-pentanediol, 3,6-dithia-1,8-octanediol, 9-oxa-3,6,12,15-tetrathia-1,17-heptadecanediol, etc., water-soluble sulfur-containing organic dibasic acids and water-soluble salts thereof such as ethylenebisthioglycollic acid and the sodium salt thereof, etc., imidazolidinethiones such as methylimidazolidinethione, etc. Further, the fixing agents described in L.F.A. Mason, *Photographic Processing Chemistry*, pages 187 to 188, Focal Press (1966) are also preferred.

The following examples are given to illustrate the present invention in more detail.

EXAMPLE 1

An aqueous silver nitrate solution and an aqueous potassium bromide solution were simultaneously added to an aqueous gelatin solution kept at 50° C. over a period of 50 minutes. During the period of addition, the pAg of the mixture was controlled at 7.9, and a silver bromide emulsion containing grains with an average size of 0.25 micron was prepared. Then, the emulsion was chemically ripened, after the soluble salts had been removed, with the addition of 43 mg of sodium thiosulfate per mol of silver bromide at 60° C. for 60 minutes. This emulsion, which contained 120 g of gelatin per mol of silver bromide, exhibits a negligible internal sensitivity compared to the external (surface) sensitivity.

To the thus-perpared silver bromide emulsion, Compound (I-2) and thioamide compound of the present invention was added as shown in Table 1 below, and then 2-hydroxy-4,6-dichloro-1,3,5-triazine sodium salt as a hardening agent was added to the emulsion. The resulting emulsion was coated on a cellulose triacetate film in a coating rate of 45 mg of silver per 100 cm$^2$. 22 photographic material samples were prepared as described above and each was exposed to light from a tungsten lamp through an optical wedge for 1 second, and then developed with a developer of the following composition at 20° C. for 5 minutes.

N-Methyl-p-aminophenol Hemisulfate: 5 g
Hydroquinone: 10 g
Sodium Sulfite (anhydrous): 75 g
Sodium Metaborate (tetrahydrate): 30 g
5-Methylbenzotriazole (1% methanol soln.): 10 ml
Potassium Hydroxide: 12 g
Water to make: 1,000 ml (pH=11.5)

The photographic characteristics obtained are shown in Table 1 below in which the value of the relative photographic speed corresponds to the reciprocal of the exposure amount required to obtain an optical density of 2.0 above fog, expressed relatively on the basis that control Sample 1 was 100. Processing after development was conducted in a conventional manner.

TABLE 1

| Sample No. | Compound I-2 (amount added) | Compound II No. | Amount* Added | Relative Photographic Speed | Gamma | Fog |
|---|---|---|---|---|---|---|
| 1 | — | — | — | 100 | 5.5 | 0.04 |
| 2 | 2.3 10$^{-2}$ | — | — | 210 | 18 | " |
| 3 | " | II-1 | 4.3×10$^{-4}$ | 550 | >20 | " |
| 4 | " | " | 1.3×10$^{-3}$ | 890 | " | " |
| 5 | " | II-2 | 1.0×10$^{-3}$ | 310 | 19 | " |
| 6 | " | " | 2.6×10$^{-3}$ | 870 | >20 | " |
| 7 | " | II-6 | 1.0×10$^{-3}$ | 440 | " | " |
| 8 | " | II-7 | 4.3×10$^{-4}$ | 450 | " | " |
| 9 | " | II-8 | 4.8×10$^{-4}$ | 840 | " | " |
| 10 | " | II-11 | 1.0×10$^{-3}$ | 450 | " | " |
| 11 | " | II-22 | 2.6×10$^{-3}$ | 365 | " | " |
| 12 | " | II-12 | 1.3×10$^{-3}$ | 280 | " | " |
| 13 | " | " | 4.3×10$^{-3}$ | 720 | " | " |
| 14 | " | II-14 | 4.3×10$^{-4}$ | 360 | 18 | " |
| 15 | " | " | 1.3×10$^{-3}$ | 480 | " | " |
| 16 | " | " | 4.3×10$^{-3}$ | 1200 | 15 | " |
| 17 | " | II-15 | 4.3×10$^{-4}$ | 355 | >20 | " |
| 18 | " | " | 1.3×10$^{-3}$ | 410 | " | " |
| 19 | " | II-16 | 4.3×10$^{-4}$ | 230 | " | " |
| 20 | " | " | 1.3×10$^{-3}$ | 310 | " | " |
| 21 | " | II-44 | 3.4×10$^{-4}$ | 320 | " | " |
| 22 | " | II-45 | 3.4×10$^{-4}$ | 280 | 18 | " |

*mol/mol Ag

A synergistic effect in speed increase is evident from the results in Table 1 by the use of a thioamide compound in combination with a compound represented by the general formula (I), although a far lower effect in speed increase is observed with the use of the thioamide compound alone. It should also be noted that an increase of gamma was achieved at the same time.

COMPARATIVE EXAMPLE

In order to separate the speed increasing effect due to the presence of thioamide compounds alone, similar procedures as described in Example 1 were carried out except that Compound (I-2) was not used. The results obtained are shown in Table 2 below.

TABLE 2

| Sample No. | Compound II No. | Amount Added | Relative Photographic Speed | Gamma | Fog |
|---|---|---|---|---|---|
| 101 | — | — | 100 | 5.5 | 0.04 |
| 102 | II-1 | 4.3×10$^{-4}$ | 135 | " | " |
| 103 | " | 1.3×10$^{-3}$ | 132 | " | " |
| 104 | II-7 | 4.3×10$^{-4}$ | 138 | " | " |
| 105 | II-12 | 1.3×10$^{-3}$ | 102 | " | " |
| 106 | " | 4.3×10$^{-3}$ | 107 | " | " |
| 107 | II-14 | 4.3×10$^{-4}$ | 145 | " | " |
| 108 | " | 1.3×10$^{-3}$ | 178 | " | " |
| 109 | " | 4.3×10$^{-3}$ | 240 | " | " |
| 110 | II-15 | 4.3×10$^{-4}$ | 91 | " | " |
| 111 | " | 1.3×10$^{-3}$ | " | " | " |
| 112 | II-16 | 4.3×10$^{-4}$ | " | " | " |
| 113 | " | 1.3×10$^{-3}$ | 78 | " | " |
| 114 | II-44 | 3.4×10$^{-4}$ | 126 | " | " |

From the results shown in Table 2 above, it can be seen that when the thioamide compound was used alone, some of the thioamide compounds provided a slight increase in photographic speed. However, when the thioamide compound was used in combination with the compound represented by the general formula (I), a marked increase in photographic speed was obtained as shown in Table 1. Moreover, even though some of the thioamide compounds (such as Compounds II-15, II-16 in Table 2) caused a decrease in photographic speed to occur, when these thioamide compounds were used in combination with the compound represented by the general formula (I), an increase in photographic speed was obtained.

EXAMPLE 2

Compound (I-2) was added to a silver bromide emulsion prepared in the same manner as in Example 1. Further, one of Compounds (II-1), (II-20), (II-22), (II-7), (II-6), (II-27), (II-28), (II-30) or (II-31) was incorporated into the emulsion as in Table 3, and finally 2-hydroxy-4,6-dichloro-1,3,5-triazine sodium salt was added to form a coating mixture, which was coated as in Example 1.

After exposure to light from a tungsten lamp through an optical wedge for one second, each sample was developed with a developer having the following composition at 20° C. for 5 minutes, and the subsequent processing was performed conventionally.

N-Methyl-p-aminophenol Hemisulfate: 5 g
Hydroquinone: 10 g
Sodium Sulfite (anhydrous): 75 g
Sodium Metaborate (tetrahydrate): 30 g
5-Methylbenzotriazole (1% methanol soln.): 10 ml
Potassium Hydroxide: 10 g
Water to make: 1000 ml (pH=11.1)

The observed photographic charactertistics are shown in Table 3 below.

TABLE 3

| Sample No. | Compound I-2 Amount Added | Thioamide Compound (II) Compound No. | Thioamide Compound (II) Amount* Added | Gamma | Relative Photographic Speed |
|---|---|---|---|---|---|
| 23 | — | — | — | 4.5 | 100 |
| 24 | $2.3 \times 10^{-2}$ | — | — | 10.0 | 165 |
| 25 | " | II-1 | $3.3 \times 10^{-4}$ | 18 | 204 |
| 26 | " | " | $1.0 \times 10^{-3}$ | 17 | 214 |
| 27 | " | II-20 | $3.3 \times 10^{-5}$ | 19 | 170 |
| 28 | " | " | $1.0 \times 10^{-4}$ | 16 | 160 |
| 29 | " | II-22 | $3.3 \times 10^{-4}$ | 16 | 190 |
| 30 | " | " | $1.0 \times 10^{-3}$ | 16 | 200 |
| 31 | " | II-7 | $3.3 \times 10^{-4}$ | 18 | 195 |
| 32 | " | " | $1.0 \times 10^{-3}$ | 18 | 204 |
| 33 | " | II-26 | $1.0 \times 10^{-4}$ | 20 | 195 |
| 34 | " | " | $2.0 \times 10^{-4}$ | 18 | 224 |
| 35 | " | " | $4.1 \times 10^{-4}$ | 18 | 340 |
| 36 | " | II-27 | $1.0 \times 10^{-4}$ | 16 | 270 |
| 37 | " | " | $2.0 \times 10^{-4}$ | 15 | 347 |
| 38 | " | " | $4.1 \times 10^{-4}$ | 15 | 407 |
| 39 | " | II-29 | $1.0 \times 10^{-4}$ | 14 | 240 |
| 40 | " | " | $2.0 \times 10^{-4}$ | 13 | 270 |
| 41 | " | " | $4.1 \times 10^{-4}$ | 13 | 372 |
| 42 | " | II-40 | $1.0 \times 10^{-4}$ | 14 | 190 |
| 43 | " | II-38 | $1.0 \times 10^{-4}$ | 15 | 230 |
| 44 | " | " | $2.0 \times 10^{-4}$ | 14 | 240 |
| 45 | " | " | $4.1 \times 10^{-4}$ | 14 | 260 |

*mol/mol Ag

As is evident from the results in Table 3, development at a lower pH, i.e., a less active developer compared with that employed in Example 1, resulted in a marked increase in gamma for the samples containing both a compound represented by the general formula (I) and a thioamide compound in comparison with the samples containing only the compound represented by the general formula (I) alone.

Speed increases were also observed. Achieving such a high gamma by the use of a rather inactive and hence stable developer has not been known until now.

EXAMPLE 3

Sample No. 1 which did not contain Compound (I-2) for comparative purposes and Sample No. 2 which contained Compound (I-2) in an amount of $2.3 \times 10^{-2}$ mol per mol of Ag of Example 1 were developed with a series of developers, each of which contained one of Compounds (II-1), (II-2), (II-14) or (II-44) added to the developer composition shown in Example 1 at 20° C. for 5 minutes. The results obtained are shown in Table 4 below.

TABLE 4

| Thioamide Compound No. | Amount Added to Developer | Sample No. 2 Speed | Sample No. 2 Gamma | Sample No. 2 Fog | Sample No.1 Speed | Sample No.1 Gamma | Sample No.1 Fog |
|---|---|---|---|---|---|---|---|
| — | — | 210 | 18 | 0.04 | 100 | 5.5 | 0.04 |
| II-1 | $2.3 \times 10^{-5}$ | 300 | 18 | " | 105 | " | " |
| II-1 | $2.7 \times 10^{-4}$ | 501 | 18 | " | 129 | " | " |
| II-1 | $8.2 \times 10^{-4}$ | 575 | 19 | " | 132 | " | " |
| II-1 | $2.7 \times 10^{-3}$ | 630 | 19 | " | 150 | " | " |
| II-12 | $2.3 \times 10^{-5}$ | 580 | 18 | " | 120 | " | " |
| II-14 | $2.3 \times 10^{-5}$ | 350 | 18 | " | 102 | " | " |
| II-44 | $2.3 \times 10^{-5}$ | 420 | 18 | " | 115 | " | " |

It is apparent from the results in Table 4 above that only a slight increase in speed was obtained by developing Sample No. 1 which did not contain a compound represented by the general formula (I) with a developer containing a thioamide compound. However, when Sample No. 2 which contained a compound represented by the general formula (I) was developed with a developer containing a thioamide compound, remarkably high increases in speed were obtained.

While the invention has been described in detail and with reference to specific embodiments thereof, it will be apparent to one skilled in the art that various changes and modifications can be made therein without departing from the spirit and scope thereof.

What is claimed is:

1. A method for forming a negative photographic image comprising (i) image-wise exposing a photographic light-sensitive material comprising a support having thereon at least one silver halide mono-disperse photographic emulsion layer containing surface latent images silver halide grains and at least one compound represented by the following general formula (I):

$$R^1NHNHCOR^2 \quad (I)$$

in an amount of about $10^{-5}$ to about $10^{-1}$ mol/mol Ag, wherein $R^1$ represents an aryl group, $R^2$ represents a hydrogen atom, a phenyl group, or an unsubstituted alkyl group having 1 to 3 carbon atoms; in said photographic emulsion layer or in another hydrophilic colloid layer, and (ii) developing said exposed material with a developing solution containing a developing agent which is an aminophenol, a 3-pyrazolidone, a 1-phenyl-3-pyrazoline, a dihydroxybenzene or a mixture of a dihydroxybenzene and other of said afore-mentioned developing agents, and containing about 0.15 mol/liter or more of a sulfite ion and having a pH of about 10.5 to 12.3, wherein a compound having a thioamido moiety in the molecular structure thereof is present in an emulsion, an auxiliary layer, a developing solution or a prebath, as an agent which increases sensitivity and contrast, wherein said compound having a thioamido moiety in the molecular structure thereof is represented by the following general formula (II):

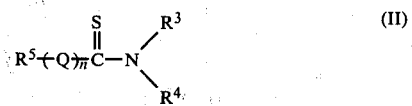

wherein $R^5$ represents a hydrogen atom, an alkyl group, an aryl group or a heterocyclic group; and Q represents a sulfur atom, a selenium atom, an oxygen atom, a disulfide group, —NR$^6$—,

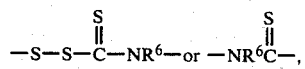

where $R^6$ has the same meaning as $R^5$; $R^3$ and $R^4$, which may be the same or different, each represents a hydrogen atom, an alkyl group, an aryl group, a heterocyclic group or an amino group; and $R^5$ and $R^6$, $R^3$ and $R^4$ or $R^3$ and $R^5$ together may combine to form a 5- or 6-membered heterocyclic group provided that neither of $R^4$ nor $R^6$ represents a hydrogen atom when $R^3$ and $R^5$ combine to form a 5- or 6-membered heterocyclic group and n is 0 or 1.

2. The method of claim 1, wherein $R^1$ represents an unsubstituted aryl group or an aryl group substituted with one or more of an alkyl group having 1 to 20 carbon atoms, an aralkyl group having 1 to 3 carbon atoms in the alkyl moiety thereof, an alkoxy group having 1 to 20 carbon atoms, an amino group which may be mono- or di-substituted with an alkyl group having 1 to 20 carbon atoms, an aliphatic acylamino group having 2 to 21 carbon atoms and an aromatic acylamino group, and $R^2$ represents a hydrogen atom, a methyl group, a phenyl group or a phenyl group substituted with one or more of a halogen atom, a cyano group, a trifluoromethyl group, a carboxy group or a sulfo group.

3. The method of claim 1, wherein $R^1$ represents a phenyl group or a tolyl group and $R^2$ represents a hydrogen atom or a methyl group.

4. The method of claim 1, wherein $R^1$ represents an unsubstituted aryl group or an aryl group substituted with one or more of an alkyl group having 1 to 20 carbon atoms, an aralkyl group having 1 to 3 carbon atoms in the alkyl moiety thereof, an alkoxy group having 1 to 20 carbon atoms, an amino group which may be mono- or di-substituted with an alkyl group having 1 to 20 carbon atoms, an aliphatic acylamino group having 2 to 21 carbon atoms and an aromatic acylamino group, and $R^2$ represents a hydrogen atom.

5. The method of claim 1, wherein the compound having a thioamido moiety in the molecular structure is represented by the following general formula (IIa):

wherein $Q^1$ represents the atoms necessary to complete a 5- or 6-membered heterocyclic ring, $R^{4'}$ represents an alkyl group, an aryl group or a heterocyclic group and a hydrogen atom is not bonded to the atom adjacent the thioketo group in $Q^1$.

6. The method of claim 5, wherein the heterocyclic ring completed by $Q^1$ is selected from the group consisting of a thiazoline ring, a thiazolidine ring, a selenazoline ring, an oxazoline ring, an oxazolidine ring, an imidazoline ring, an imidazolidine ring, a pyrazoline ring, a pyrazolidine ring, a 1,3,4-thiadiazoline ring, a 1,3,4-oxadiazoline ring, a 1,3,4-triazoline ring, a tetrazoline ring, a thiohydantoin ring, a rhodanine ring, a dihydropyridine ring, a dihydropyrimidine ring, a dihydrotriazine ring, a benzothiazoline ring, a naphthothiazoline ring, a dihydronaphthothiazoline ring, a tetrahydrobenzothiazoline ring, a benzoselenazoline ring, benzoxazoline ring, a naphthoxazoline ring, a benzimidazoline ring, a dihydroimidazolopyrimidine ring, a dihydrotriazolopyridine ring, a dihydrotriazolopyrimidine ring, a dihydropyrazolopyridine ring, a dihydropyrazolopyrimidine ring, a dihydropyrazolopyrimidine ring, a dihydropyrrolopyrimidine ring, and a dihydrotriazolopyrimidine ring.

7. The method of claim 6, wherein the heterocyclic ring completed by $Q^1$ is unsubstituted heterocyclic ring.

8. The method of claim 6, wherein the heterocyclic ring completed by $Q^1$ have one or more substituent selected from the group consisting of an alkyl group, an alkoxy group, an alkylthio group, a hydroxy group, a mercapto group, an amino group which may be mono- or disubstituted, an aryl group, an alkenyl group, an aralkyl group, a halogen atom, a cyano group, a carboxy group, a sulfo group, a carbamoyl group which may be substituted, a thiocarbamoyl group which may be substituted, an alkoxycarbonyl group, an aryloxycarbonyl group, an alkylcarbonyl group, and an oxo atom.

9. The method of claim 6, wherein the heterocyclic ring completed by $Q^1$ contains a divalent substituent selected from the group a thioxo group, a benzylidene group, an ethylidene group, a substituted ethylidene group and a heterocyclic divalent residue.

10. The method of claim 1, wherein the compound having a thioamido moiety in the molecular structure thereof is a compound selected from the group consisting of:
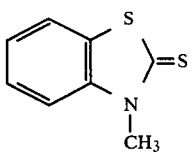
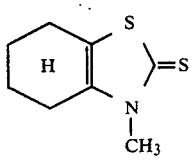
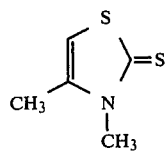
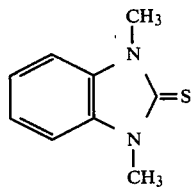
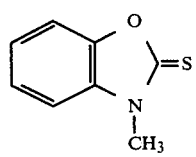
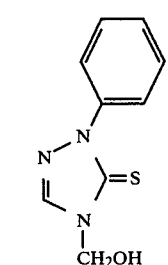
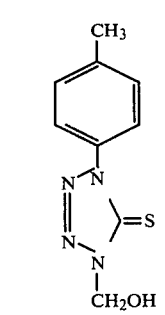
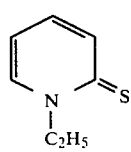
-continued
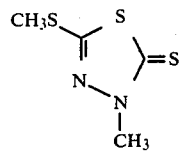
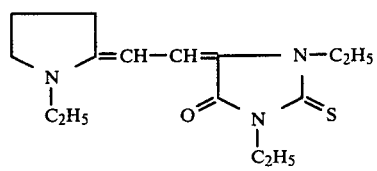
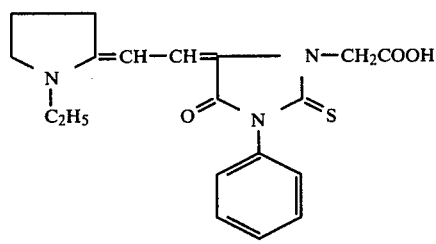
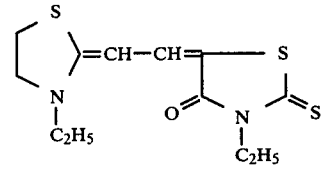
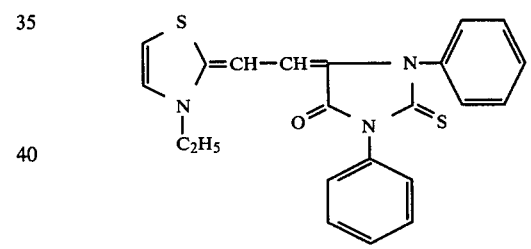
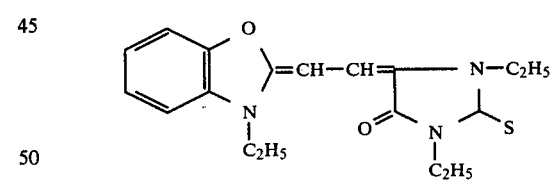
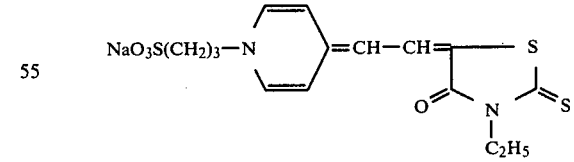
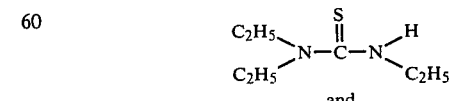
and
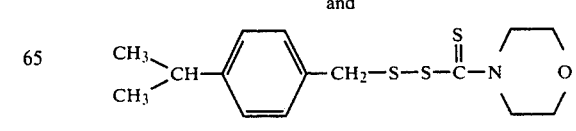

11. The method of claim 3 or 9, wherein in the development processing the development of the photographic material is carried out at a pH of about 11.0 to about 12.3.

12. The method of claim 1, wherein said silver halide grains have an average grain size of about $0.7\mu$ or less.

13. The method of claim 1, wherein said silver halide emulsion contains about 20 g to about 250 g of binder per mol of silver halide.

14. The method of claim 1, wherein said dihydroxybenzene is hydroquinone.

15. The method of claim 1, wherein said compound of general formula (I) is present in an amount of $5 \times 10^{-4}$ to $5 \times 10^{-2}$ mol/mol/Ag.

16. The method of claim 1, wherein said compound of general formula (II) if present in said element is present in an amount of about $10^{-6}$ to about $5 \times 10^{-2}$ mol/mol/Ag in an equivalent coated area and, if present is said developer, is present in an amount of about $10^{-7}$ to about $10^{-2}$ mol/liter.

17. The method of claim 16, wherein said compound of general formula (II) if present in said element is present in an amount of about $3 \times 10^{-5}$ to about $10^{-2}$ mol/mol Ag in an equivalent coated area and, if present in said developer, is present in an amount of about $3 \times 10^{-6}$ to about $5 \times 10^{-3}$ mol/liter.

18. The method of claim 16, wherein said material comprises coated silver in an amount of about 0.5 g/m$^2$ to about 10 g/m$^2$ of said support.

19. The method of claim 17, wherein said material comprises coated silver in an amount of about 0.5 g/m$^2$ to about 10 g/m$^2$ of said support.

20. The method of claim 1, wherein said at least one compound represented by the general formula (I) does not substantially function as a developing agent.

21. The method of claim 1, wherein said developing agent consists essentially of hydroquinone.

22. The method of claim 1, wherein said developing agent is a mixture of hydroquinone and aminophenol.

* * * * *